United States Patent [19]

Millner

[11] Patent Number: 5,123,841
[45] Date of Patent: Jun. 23, 1992

[54] INTERPROXIMAL DENTAL PLAQUE REMOVER

[76] Inventor: Don E. Millner, 212 Bruce Rd., Washington Crossing, Pa. 18977

[21] Appl. No.: 503,054

[22] Filed: Apr. 2, 1990

[51] Int. Cl.$^5$ .................. A61C 3/06; A61C 15/00; A61H 7/00
[52] U.S. Cl. .................. 433/125; 128/62 A; 132/322
[58] Field of Search .......... 128/62 A; 433/125; 15/167.1, 167.2, 167.3, 22.1; 132/309, 321, 329

[56] References Cited

U.S. PATENT DOCUMENTS

| | | | |
|---|---|---|---|
| 2,004,633 | 6/1935 | Miller | 15/167.1 |
| 3,183,538 | 5/1965 | Hubner | 128/62 A |
| 3,466,689 | 9/1969 | Aurelio et al. | 15/22.1 |
| 3,552,022 | 1/1971 | Axelsson | 433/122 |
| 3,934,298 | 1/1976 | Kim | 15/167.1 |
| 4,051,571 | 10/1977 | Ayers | 15/167.1 |
| 4,222,143 | 9/1980 | Tarrson et al. | 132/321 |
| 4,729,142 | 3/1988 | Yoshioka | 128/62 A |
| 4,880,382 | 11/1989 | Moret et al. | 128/62 A |

Primary Examiner—John G. Weiss
Assistant Examiner—Nicholas D. Lucchesi
Attorney, Agent, or Firm—William L. Muckelroy; Iman Abdallah

[57] ABSTRACT

A device for removal of dental plaque from the furca, cemento-enamel junction, and gingival pockets in between two adjacent teeth, the device having a dental arm with a detachable dental brush having a malleable spine supported substantially perpendicular from the arm, the arm imparting a tiny mechanical vibratory action from a motor driving an eccentrically mounted cylindrical weight through contact of the brush with the furca, junctions and pockets in between the adjacent teeth. The brush having a conical shape defined by a cross section representing an isoceles triangle having an apex angle of approximately 30° wherein the surface of the brush is contourable and the bristles are splayed by the tiny vibratory action into the furca, junctions, and pockets.

10 Claims, 5 Drawing Sheets

FIG. 1
FIG. 2A
FIG. 2B
FIG. 2C
FIG. 2D
FIG. 2E
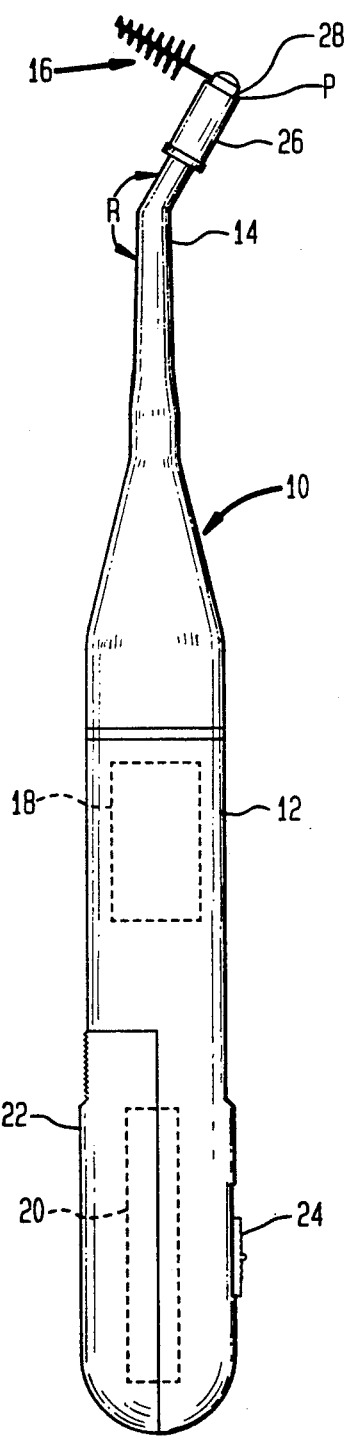
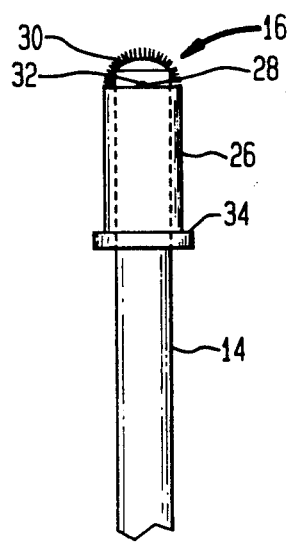
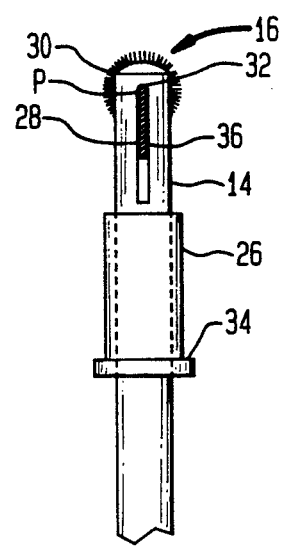
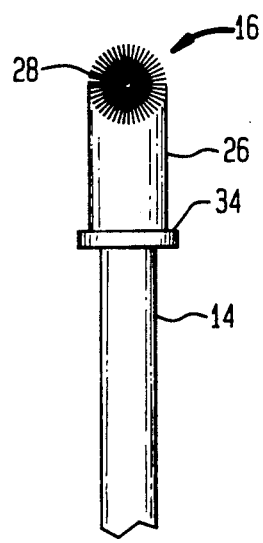
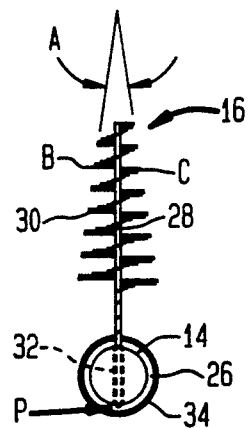
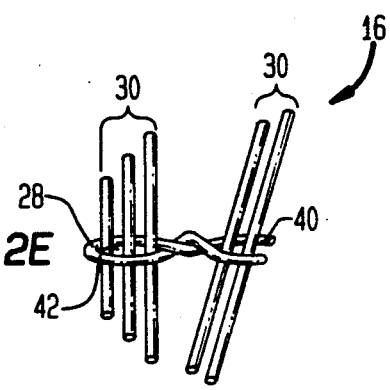

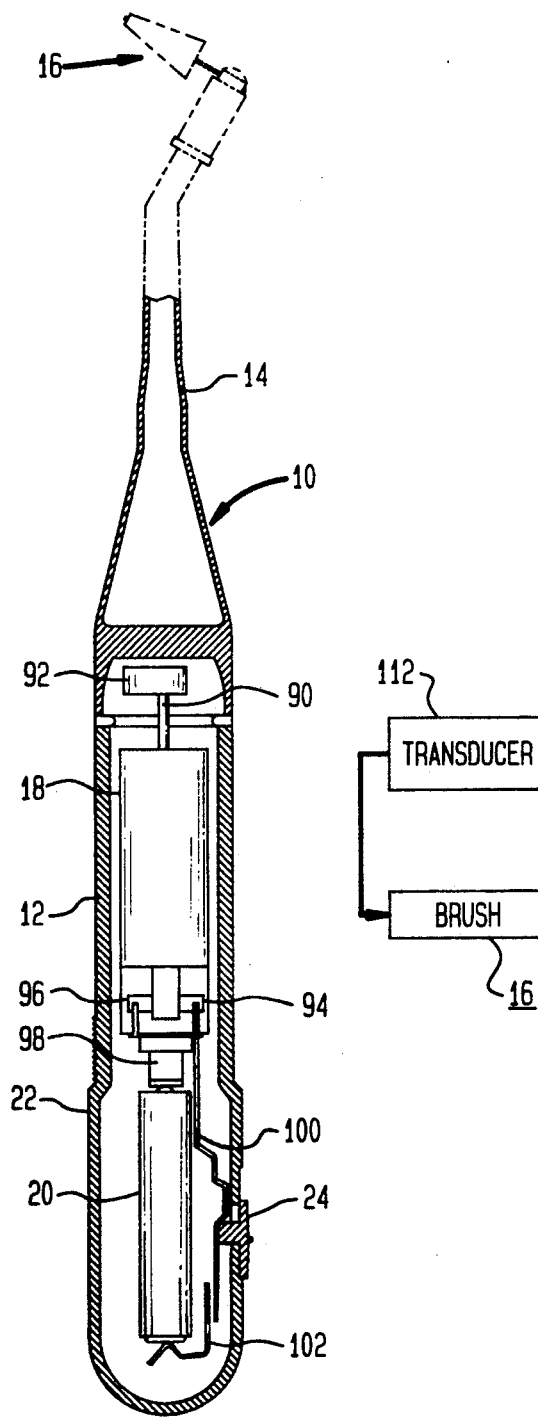
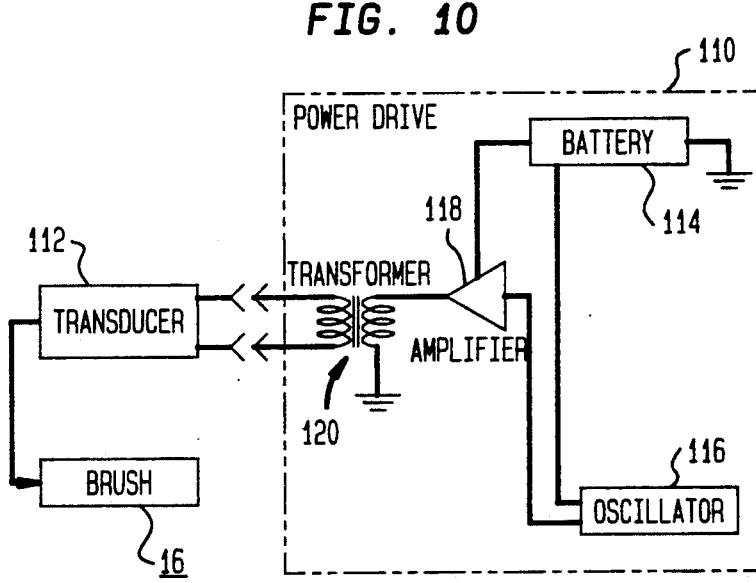

INTERPROXIMAL DENTAL PLAQUE REMOVER

BACKGROUND OF THE INVENTION

1. Field Of The Invention

This invention is related to dental hygiene and more particularly to a dental apparatus which can clean in between two teeth below the gum line, down the furca, and along the surface junctions of tooth implants using a conical brush and a mechanical vibratory action of the brush while inserted in between two teeth.

2. Description Of The Prior Art

To treat and prevent periodontal disease, as well as avoid root surface, and inter-proximal cavities, it is necessary to have a regular program of dental oral hygiene. Numerous apparatus have been promoted to serve as prophylactic devices for preventing dental problems. Brushing and flossing of the teeth are well known prophylactic techniques, but are insufficient to throughly clean and protect the teeth. Irrigation apparatus are also available which serve to wash away toxins produced by dental plaque. However, they do not remove the dental plaque itself, especially dental plaque located inter-proximally, between the teeth, in the furca and below the gum line, even using a pulsating action with the irrigating apparatus. This is insufficient to remove the dental plaque located in the furca, below the gum line in between the teeth. This technique does not provide adequate dental prophylactic.

Many types of chemical agents are on the market for removal of bacterial accumulations from the teeth. Plax TM is an example. Most of these, however, also produce unwanted side effects. Even when these chemical agents are used in a more mild form, they are still not effective for plaque removal. They are, however, effective for retarding the re-growth of bacterial plaque after it has been removed from the tooth surface by brushing or other means.

More professional equipment is available for use by dentists via inter-connection to various dental apparatus. For example, U.S. Pat. No. 3,552,022 describes an apparatus which is connected to the dental drill having a tool which reciprocates and carries out a mechanical cleaning of the teeth by mechanical or frictional engagement in order to remove the dental plaque. Such instrumentation is, however, complex, and must be utilized by dental specialists under office conditions. It does not provide for self use on a daily basis.

U.S. Pat. No. 4,735,200 issued on Apr. 5, 1988 to Westerman does provide an oral hygiene apparatus for daily use wherein a dental hand piece supports a replaceable dental bit which can also comprise a brush. The dental bit or brush is operated by a fluid actuated driving mechanism in the hand piece causing reciprocation of the dental bit or brush to effect a mechanical cleaning action on contact with dental surfaces. The dental tip envisioned by Westerman is either a rigid tip or a brush type tip which can either be smooth or include abrasive surfaces. Westerman also suggests the use of different shapes for the brush to permit its utilization on inter-proximal surfaces. Westerman does not suggest or disclose details of construction of his dental brush or a particular construction of the brush adaptable for removal of plaque from the furca.

In U.S. Pat. No. 4,787,847 issued to Martin, et al in 1988 the general problem and necessity of a dental hygiene apparatus for removal of plaque as a means of treating, preventing or limiting periodontal disease is addressed. Martin discloses a method and apparatus for immobilizing sub-gingival bacteria and for removing soft plaque from accessible surfaces of the teeth on a substantially daily basis. Martin discloses the use of piezoelectric transducer to generate low energy vibrations and for applying these vibrations to the teeth and gingival fluids to cause mild cavitation within the fluid to remove some sub-gingival plaque. However, Martin, et al and the foregoing references do not address the problem of a means for daily removal of plaque from the furca and other inter-proximal dental spaces in the oral cavity at home.

SUMMARY OF THE INVENTION

The novel invention allows the daily sweeping of a plenum defined by the cavity in between adjacent teeth and daily sweeping of the furca and subgingival areas in between teeth such that plaque is disrupted and dislodged from these areas. The normal flushing action of the mouth and gingival crevices subsequently removes the mobilized bacteria and plaque from the gingival areas thus eliminating one of the causes of periodontal diseases, namely the growth of bacteria and formation of layered plaque in subgingival pockets, furca, at the cemento-enamel junction (CEJ) and at surface junctures of implants interproximal to the teeth.

The invention achieves this objective by utilizing tiny vibrations to move bristles of a brush having a malleable spine. The brush must have bristles displaying a conical shape wherein the cross section of the conical shape displays an isoceles triangle having an apex angle of approximately 30°. The brush is mobilized by a DC electric motor which transmits mechanical vibrational energy to the brush by means of rotating an eccentrically mounted cylindrical weight. The vibrations caused by the eccentric rotation of the cylindrical weight causes an arm of the interproximal dental plaque remover to vibrate very small distances (0.5 mm to 3 mm) at frequencies in the subaudio range. These vibrations are transferred from the arm to the interproximal conical shaped brush when inserted between two teeth to disrupt and dislodge plaque and thereby interrupt and limit the process of plaque colony maturation. The vibration is harmless to the surrounding gum tissue. Thus, the novel interproximal dental plaque remover may be safely and easily used at home on a daily basis to prevent and/or retard the development of pathogenic bacterial flora and/or the formation of calculus (hardened plaque) which, when formed, would otherwise require removal by professional dental personnel using scaling, ultrasonic and other high energy devices.

The arm is rigidly mounted on the dental plaque remover. The arm receives mechanical energy from the eccentrically mounted cylindrical weight which eccentrically rotates in an enlarged cylindrical chamber such that the change in the momentum of the weight in the chamber thus causes the arm to vibrate. The motor is firmly attached to the handle of the plaque remover which also contains a 1.5 volt battery and combination slide and contact switch for interconnecting the battery to the motor. Alternatively, a push button switch may be used. The conical brush is fixed by means slidably mounted on the arm which engages a portion of the spine of the brush. Vibration of the brush after insertion into an interproximal cavity causes splaying of the bristles of the brush into the CEJ and subgingival areas and into the furca of individual teeth. This splaying of the bristles of the brush disrupts adherent plaque colonies and mobilizes bacteria into the subgingival fluids without harming the surrounding soft tissue.

The spine of the brush is made of this malleable twisted wire coated with an enamel. The malleability of the spine of the brush permits it to be bent along the curvature of a tooth during the hundreds of vibratory strokes. This action insures that the brushes are splayed into cavities formed at the juncture between a tooth and the surrounding gum tissue. This vibrational splaying disrupts plaque formed in any subgingival and supragingival areas into which the ends of bristles of the conical brush splay or unfold.

The novel vibrating conical brush provides tunneling, penetration and splaying into the furca. This in combination with the malleability of the spine of the brush and actual bending of the spine during use cause the brush to effectively penetrate into the hidden gingival crevices, CEJ and furca. With daily use, the novel interproximal dental plaque remover with the conically shaped brush becomes increasingly more comfortable to the patient. This is due to an increase in the size of the interproximal plenum which results from decreased tissue inflammation. This daily use manifests a remarkable dimunition of the irritants responsible for the occluding inflammatory tissue.

The objective of this invention relates back to U.S. Pat. No. 3,466,689 issued to Aurelio, et al on Sept. 16, 1969 for a "Sonic Energy Dental Cleaning Device". This patent describes a power driven appliance adapted for oral use in cleaning the teeth comprising a source of vibratory energy in the sonic range disposed in vibration transmitting relation within a casing having a parabolic nose cone onto which a tooth brushing attachment was removably attached.

Aurelio pointed out that it had previously been proposed to utilize vibratory energy in the sonic range and a power driven tooth brush (referring to Hubner's U.S. Pat. No. 3,183,538 which described a portable electric toilet apparatus which utilized a motor driven excentrically as a vibratory energy source).

Other sonic and ultrasonic tooth brushing means exist in the prior art, for example, the ultrasonic kit and motor systems devised by Balamuth, et al in U.S. Pat. No. 3,809,977 issued on May 7, 1977. On Dec. 4, 1979 Hatter, et al was issued U.S. Pat. No. 4,176,454 for an ultrasonic tooth cleaner specifically adapted for removing dental plaque from teeth. Cleaning is effectuated by liquid coupling of the teeth to an ultrasonic generator. The critical aspect of inter-proximal cleaning and the problems associated with attaining access are not addressed in the above prior art.

In 1982 Kuris was issued U.S. Pat. No. 4,333,197 for an ultrasonic tooth brush. This was an adaptation and modification of his earlier ultrasonic tooth brush as disclosed in U.S. Pat. No. 4,192,035 issued in 1980. In 1984 Fattaleh was issued U.S. Pat. No. 4,432,729 for an oral hygiene device wherein the cleaning head is driven in an oscillatory manner.

OBJECTS OF THE INVENTION

The novel apparatus is designed to treat periodontitis caused by the formation of plaque. The earliest clinical signs of periodontitis are usually color and texture changes and slight enlargement of the gingiva with some loss of firmness and adaptation to the teeth. The disease may remain in this state or may progress to the loss of attachment of gingiva to the tooth and the formation of periodontal pockets. The pockets continue to harbor bacterial plaque and in time become deeper making this pocketed plaque inaccessible using the oral hygiene procedures of the prior inventions disclosed herein. Left untreated, the condition worsens, supporting tissue and bone are destroyed and the unsupported tooth is lost. Despite the presence of deep-seated disease, the marginal tissues may have a deceptively healthy appearance.

An object of the novel device is to control bacterial plaque. This is essential for long-term successful treatment of patients with periodontal disease. Cleansing devices such as a tooth brush and dental floss that mechanically reach and disrupt the bacterial plaque are indispensable. However, more thorough mechanical means of disrupting the bacterial plaque located interproximally along the furca are needed and desired by practitioners for patients. There are, until now, no automatic brush devices that can prevent the formation of or that disrupt already formed bacterial plaque along the furca for use by out-patients daily.

The choice of therapy depends on the state of the disease. In the early stages practitioners desire a mechanical approach to inter-proximal dislodgement of pockets of bacterial plaque along the tooth furca and at the irregular surfaces exhibited by implants. In the early stages mechanical disruption with a tool that can be used on a daily basis by a patient is the approach most desired. A major object of the novel device is a mechanical device that insures disruption and dislodgement of bacteria along the furca as well as along the cement-enamel junction or "CEJ". This is desirable especially with gingivitis and early periodontitis with loss of attachment (pocket formation) of 3-4 millimeters. Heretofore these diseases have usually been treated by scaling and root planing combined with effective chemical plaque control. However, effective plaque control in this way is difficult for the patient on a daily basis.

Heretofore a manual mechanical inter-proximal brush has been used but with limited success because the number of strokes that can be applied mechanically by a patient is many hundreds of times less than that which can be applied by a novel electrically operated, mechanically vibrating inter-proximal brush and, the manual strokes were always too long distance-wise, to allow the bristles to splay. Thus, a key object of the novel device is to provide a means for very tiny stroke lengths a few hundred times over a few minutes. Manual strokes on a microscopic level are similar to an arrow being pulled or pushed through a cavity. All of the feathers are pushed or pulled in the same direction before reversing direction. However, a main object of the novel device is to vibrate the "feathers" or bristles in the cavity hundreds of times with tiny random movements and a burrowing action to flagellate the furcal areas with the ends of the bristles.

As the pockets deepen, scaling and root planning as well as chemical plaque control become less effective as a total treatment method especially when done intermittently. Vigorous disruption on a daily basis of the plaque formed in the pockets and furca is necessary. This is particularly true when root surfaces are irregular, grooved or furcated and when pockets are narrow and tortuous.

Yet another object of the novel invention is to reduce the necessity of periodontal pocket reduction surgery to obtain visibility and access to infected areas. The novel apparatus when used on a daily basis may obviate the necessity of complete root debridement and other surgical approaches to eliminate pockets and remove plaque and calculus which cause the deterioration of normal tissue. Heretofore periodontal surgery was necessary to establish a favorable gingival architecture when hyperplastic gingiva, gingiva cratoring or other contour problems existed. The post-surgical architecture enabled patients to perform better plaque control. Another object of the novel apparatus is to provide better post-surgical plaque control and thereby act as a post-surgery prophylactic.

Another object of the novel invention is to diminish the necessity for frequent professional tooth cleaning and to diminish the frequency of necessary visits to the dentist's office for professional care as a result of periodontal disease. The Academy of General Dentistry in a 1984 publication entitled "Etiology and Treatment of Periodontal Disease: Bacterial Aspects", indicated the best method by far to control bacterial plaque is the mechanical removal of the plaque. Moreover, when pockets are deep and torturous, that is, follow convoluted pathways around the tooth surfaces or when the pockets are deeper then five or six milimeters or if these pockets are located along root surfaces that are irregular, groved, furcated, and/or where the roots divide, it is virtually impossible for even a skilled operator to manipulate subgingival scalers and curettes with predictable thoroughness so that all of the plaque is removed and all of the calculus is removed from the tooth surface. Heretofore surgery was necessary to provide a means of access in order to do this sub-gingival scaling and cleaning centrally necessary to periodontal treatment. The novel invention addresses this problem by disrupting the plaque. Hence, yet another object is to neutralize the bacterial colonies in these hidden areas without the necessity of surgical intervention.

To understand the various objects of the novel device, from a dental practitioner's viewpoint, it should be recognized that there is a serious need to provide a daily means for removing plaque from the juncture between the bulbous overlapping crown of a tooth and its supporting underlying root. This juncture area is remote, difficult to access manually, and resembles what may be termed an arcuate cemento-enamel junction.

BRIEF DESCRIPTION OF THE DRAWINGS

FIG. No. 1 is a view of the interproximal dental plaque remover supporting a brush.

FIG. 2(a) is a partial view of the head of the interproximal dental plaque remover shown in FIG. 1(a) showing the brush construction and assembly from the rear.

FIG. 2(b) is a partial view of the interproximal brush remover shown in FIG. 1 from the rear with a retaining sleeve retracted.

FIG. 2(c) is a front view of the head and brush assembly of the device 10 as shown in FIG. 1.

FIG. 2(d) is a top view of the head and brush assembly of the device 10 shown in FIG. 1.

FIG. 2(e) shows the details of the construction of the brush according to the invention.

FIG. 7 is a partial cut-a-way view of the device shown in FIG. 1.

FIG. 10 is a circuit diagram showing an alternative sonic power drive for vibrating the brush depicted in FIG. 1.

DESCRIPTION OF THE PREFERRED EMBODIMENT

Figure 3A:
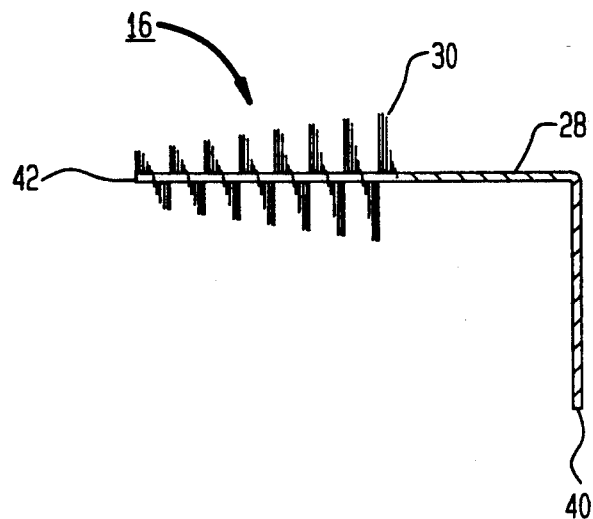
FIG. 3(a) is a side view of the brush according to the invention.

Referring now in detail to the drawings the reference numerals herein refer to like numbered parts in the various figures of the drawings, to wit:

Referring now to FIG. 1, there is shown generally a novel interproximal dental plaque remover, more particularly an electrically driven dental plaque remover or device 10 in accordance with the invention. The device 10 has a handle 12 connected to an arm 14, and a brush 16 attached to the arm 14. The device 10 is driven or energized by a DC motor 18, for example, located inside of the handle 12. The motor 18 is powered by a 1.5 volt DC battery 20 for example. Access to the battery 20 is gained by means of a slidably demountable cover 22. The battery 20 is interconnected to the DC motor 18 by means of an external slidably mounted switch 24.

The arm 14 is made of plastic. The handle 12 and arm 14 are hollow. The arm 14 is bent approximately midway through an angle R wherein R is approximately 120°. This bend facilitates orientation in and entry into the oral cavity or mouth (now shown). A slidably mounted annular piece such as, for example, retainer 26 is attached to the end of the arm 14. The retainer 26 firmly mounts the brush 16 to the arm 14 by frictionally grasping a spine 28 of the brush 16 at the portion bent parallel to the arm 14 as shown in greater detail at FIGS. 2a, 2b, 2c and 2d.

In FIG. 2a brush 16 is shown with bristles 30. The bristles 30 are bristles like those made of nylon in commonly available soft tooth brushes, for example. The spine 28 is shown extending through an aperture 32 located at the end of the arm 14. The aperture 32 is a cylindrical bore which extends perpendicularly through the arm 14. The retainer 26 has an annular rim 34 which facilitates movement of the retainer 26 slidably along the upper most portion of the arm 14.

Shown in FIG. 2b is the retainer 26 slidably demounted from the upper most end of the arm 14. As shown in FIG. 2b, a groove 36 is parallel to a central axis and extends along the length of the arm 14. The groove 36 is sized and adapted to receive a bent transverse portion of the spine 28. The spine 28 extends through the aperture 32 and is bent at a point perpendicular to the brush 16 such that the spine 28 fits into the groove 36 which is elongated and recessed. The retainer 26 may be slid upward as shown in FIGS. 2b and 2c such that it surrounds the spine 28 located in the groove 36 and thereby rigidly attaches the brush 16 to the arm 14. The rim 34 facilitates manual pushing of the retainer 26 upwards along the arm 14 so as to lock the brush 16 into place via retainment of the spine 28. FIG. 2c is a front view of the brush 16 and retainer 26 assembly mounted on the arm 14 as shown in FIG. 1. In FIG. 2d there is shown the brush 16 with the spine 28 extending therethrough and mounted onto the arm 14 by means of the retainer 26.

Shown in FIG. 2d is a top view of the brush 16 attached to the arm 14 and retained there by means of the retainer 26. The spine 28 of the brush 16 is shown extending through an aperture 32 at the upper most portion of the arm 14 and bent at a right angle to the brush 16 along the length of the arm 14, the bending beginning at the point P. The bristles 30 of the brush 16, which is 10 to 15 millimeters long, for example, are shown having a cross section resembling an isoceles triangle having an apex angle A and two equal sides B and C. This apex angle A is preferably 30°. It is critical that this angle A of the brush 16 be approximately 30°. Outside of this range the effectiveness of the brush diminishes significantly and it does not function in the manner intended as specified in this disclosure. The vibrational stroke should be approximately between 0.3 mm and 3 mm.

Usage has indicated that the apparently ideal angle A for the cross section of the conical brush 16 is where A is equal to approximately 30°. In addition, the ideal diameter of the spine 28 of the conical brush 16 shown in FIG. 2d is approximately 0.50 millimeter, for example, wherein the diameter of the wire which is twisted to make up the spindle 28 is approximately 0.25 millimeters, for example.

In FIG. 2e there is shown a detailed construction for the brush 16. The spine 28 is shown made of small diameter piece of wire 40 which is looped to form a loop 42 and then twisted wherein the various twists contain a plurality of bristles for the brush 16 rigidly therein. The wire 40 is doubled upon itself and twisted along its entire length for doubling. The wire 40 as shown is coated with an enamel paint which is selected for its non-toxicity and resistance to removal by abrasion.

Shown in FIG. 3a is a side view of the brush 16 with the spine 28 bent for mounting on the arm 14. There is shown the bristles 30 mounted onto the spine 28 in the manner shown in FIG. 2e. The spine 28 has bristles 30 attached starting at the loop 42 in the wire 40 making up the spine 28. The bristles starting at the loop 42 increase in length away from the loop 42 such that the bristles 30 form a conical shape wherein the cross section of the cone preferably has an apex angle A of 30°. The bristles extend approximately one-half the distance along spine 28. The last one-third of spine 28 is bent perpendicular to the brush 16 to facilitate mounting on the arm 14 (as shown in FIG. 1).

Figure 3B:
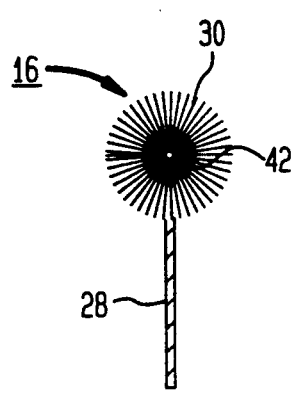
FIG. 3(b) is a front view of the conical brush according to the invention.

Shown in FIG. 3b is the brush 16, the bristles 30 and the loop 42 of the spine 28.

Figure 4:
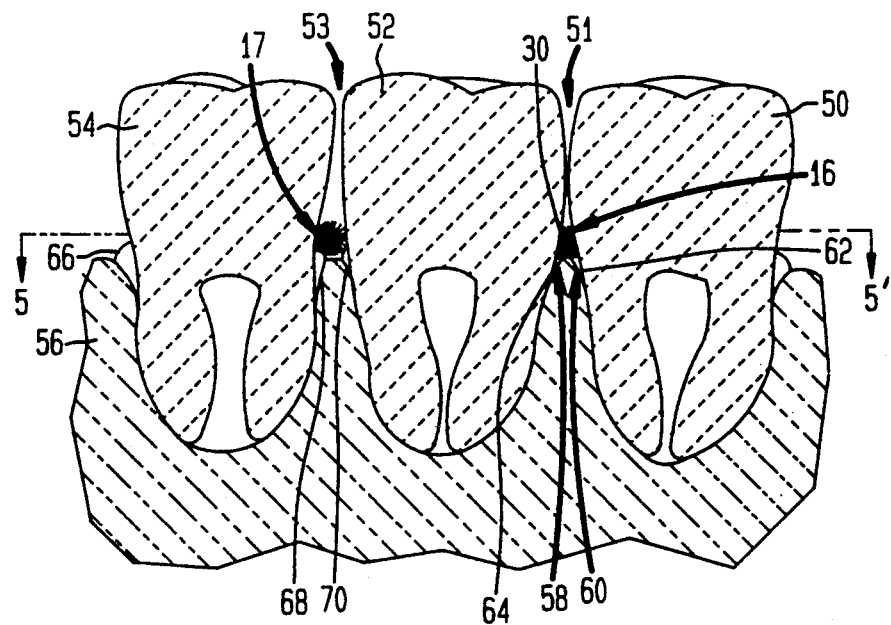
FIG. 4 is a cross sectional view of the gingival and tooth environment showing the device of FIG. 1 in use.

Referring now to FIG. 4 there is shown a cross section of a portion of an oral cavity comprising three adjacent teeth, 50, 52 and 54 mounted in a gingival structure 56. In between the teeth 50 and 52 there is shown an interproximal space 51 having inserted therein a brush 16. The brush 16 is shown with its bristles 30 splayed into cavities 58 and 60 located within the interproximal space 51 and specifically with the cavity 58 being located between the gingival tissue 56 and the side surface of the tooth 52. The cavity 60 is located between the gingival structure 56 and the side of the tooth 50. Shown within the cavities 58 and 60 are deposits 62 and 64 of plaque buildup. Splaying of the bristles 30 making up the brush 16 into the cavities 58 and 60 disrupts and dislodges the deposits 62 and 64 into the interproximal space 51 such that the deposits 62 and 64 are irrigated away by gingival fluids flowing within the interproximal space 51.

Another accumulation of plaque 66 is shown adjacent one side of the tooth 54 in a pocket formed by the adjacent gingival structure 56. For illustrative purposes other pockets of plaque 68 and 70 are shown adjacent the teeth 54 and 52, respectively, in the interproximal space 53 formed between the teeth 52 and 54.

Figure 5:
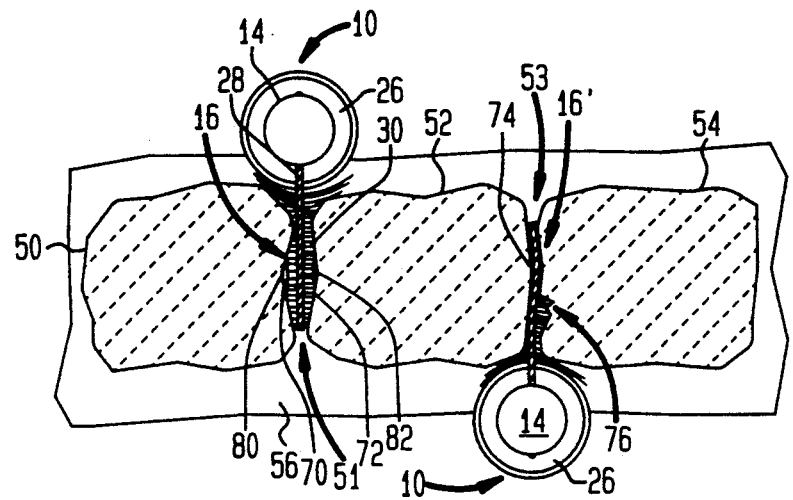
FIG. 5 is a top plan view taken along the plane 5—5' shown in FIG. 4 showing the device 10 in use in two interproximal situations.

FIG. 5 is a cross section and plan view at the plane 5—5'. The plan view shows furca 70 associated with the tooth 50 and furca 72 and 74 associated with the structure of the tooth 52. The furca 70 and 72 are penetrated by the bristles 30 of the brush 16. Vibration of the brush 16 specifically the bristles 30 within the furca 70 and 72 causes plaque located therein to dislodge and become injected into gingival fluid within the interproximal cavity 51. When the brush 16 shown in FIG. 5 is withdrawn it resembles the shape in FIG. 6a for the brush 16. Note the spine 28 is straight.

Figure 6A:
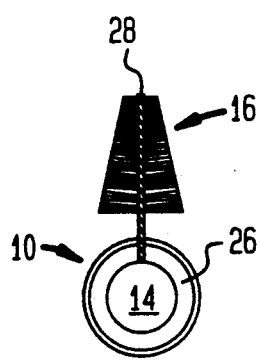
FIG. 6(a) is a top view of the device 10 showing the conical brush.
Figure 6B:
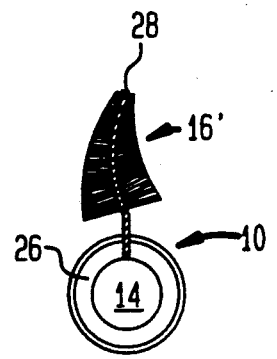
FIG. 6(b) is a top view of the device 10 showing the conical brush as contoured and modified.

A unique and novel developed feature of the brush 16 when used with an electric vibrator is specifically the transformation of the spine 28 as shown in FIG. 6a to that illustrated in FIG. 6b. The spine 28 is bent into a curved brush structure 16. By virtue of the malleability of the spine 28 the brush 16 is reformed into the altered conical structure 16'. This malleability of the spine 28 allows the brush 16 when inserted into the interproximal cavity 53 as shown in FIG. 5 to be bent by its vibrations in such a fashion as to enable it to adapt to the curvature of the furca 74 as well as the side curvature and crevices 76 associated with the tooth 54. This malleability of the spine 28 comprising the brush 16 which enables it to assume the curve structure 16' shown in FIG. 6b provides novel and critical cleaning of crevices 76 and cavity 53 associated with the tooth 54 shown in FIG. 5. This novel ability to change shape and structure after insertion into the interproximal cavity 53 and the application of vibratory energy provides a unique advantage and novel cleaning action of the interproximal space 53, the furca 74 and crevices 76 associated therewith.

As shown in FIG. 5 a dental floss line (not shown) inserted in the interproximal cavity 53 would not be able to remove plaque from the crevices 76 nor from the furca 74 located therein. Furthermore, it may be observed from FIG. 5 that a line of dental floss (not shown) inserted in the interproximal cavity 51 would be unable to remove pockets of plaque 80 and 82 located in the furca 70 and 72, respectively. The dental floss would extend across the high points but not extend into proximal crevices of the tooth 50 and not touch the plaque 80 in the furca 70. Moreover, dental floss passed in between the interproximal cavity 51 would touch the rounded areas near the cheek side and tongue side of the tooth 52 but would not be able to reach inside the furca 72 to remove the pocket of plaque 82 located in the furca 72.

The brush 16 shown in FIG. 1 is caused to vibrate and its bristles 30 are caused to splay into subgingival crevices and furca (illustrated in FIG. 4) by means of a vibrating action generated by a DC motor 18 located in the device 10. This is illustrated in detail in FIG. 7. Shown there is a DC motor 18 with a protruding shaft 90 which is caused to rotate at between 10 cps and 40 cps. Rigidly mounted on the shaft 90 in an eccentric manner is a cylindrical heavy mass 92 which when the shaft 90 rotates the eccentricity of the movement of the mass 92 causes the entire structure to vibrate, especially the arm 14, with the brush 16 attached thereto.

The arm 14 is made of plastic along with the handle 12 of the device 10. The cylindrical mass 92 weighs approximately one quarter to one half ounce and the DC motor generates power in the range of 1/25 horsepower to 1/10 horsepower. The motor is a standard conventional motor available from multiple suppliers in the U.S. and from Taiwan. The DC motor 18 has a negative contact 94 and a positive contact 96. The positive contact 96 is directly connected to the positive post of the battery 20 by means of a metallic conducting interconnector 98. The negative contact 94 is interconnected to the negative side of the battery 20 by means of a metallic interconnecting strip 100 which interconnects to the negative post of the battery 20 by being pressed against another metallic strip interconnector 102 when the slide switch 24 is pushed upwards towards the brush 16 and arm 14.

Figure 8:
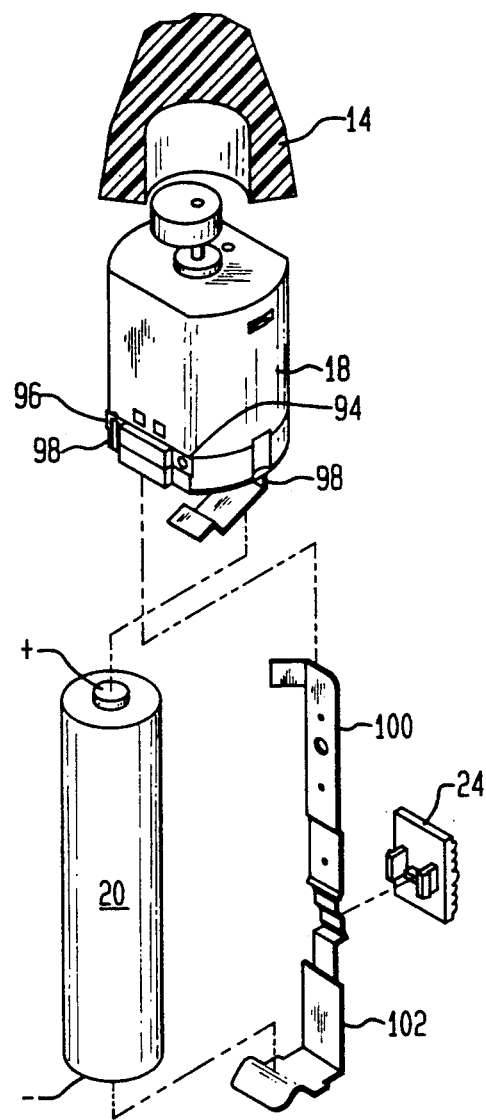
FIG. 8 is a perspective exploded view of the internal components of the device 10 shown in FIG. 7.

Shown in FIG. 8 is the interconnector 98 which interconnects the positive terminal 96 of the motor 18 to the positive terminal of the battery 20.

Figure 9:
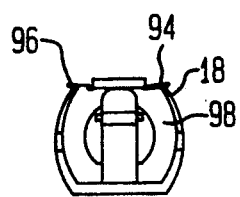
FIG. 9 is a bottom view of the motor and inter-connector assembly.

Shown in FIG. 9 is a bottom view of the motor 18 as shown in FIG. 8. There is shown the interconnector 98 in the manner it is attached beneath the motor 18. The interconnector 98 is shown connected to the positive terminal 96 of the motor 18. The negative terminal 94 is also shown. The interconnector 98 is fashioned so as to be spring loaded against the positive terminal of the battery 20.

In FIG. 10 an alternative embodiment of a power source for vibrations for the device 10 is shown. There a power drive 110 for energizing the device 10 with a low frequency transducer 112 longitudinally located in the arm 14. The power drive 110 shown in FIG. 10 is located in the handle 12. The power drive 110 has a DC power supply, for example, a battery 114, to energize an oscillator 116 and an amplifier 118. The oscillator 116 produces a sinusoidal signal at a desired operating frequency for the transducer 112. The transducer 112 is located in the arm 14 and via the arm 14 power is transmitted to the brush 16 which then vibrates. More specifically, the power drive 110 uses as a source of power, a battery 114 which drives an amplifier 118 as well as an oscillator 116. The signal from the oscillator 116 is amplified by the amplifier 118 and fed to a transformer 120. The output from the transformer 120 is directed to the transducer 112. The amplifier 118 amplifies the oscillator signal and introduces the signal to the primary winding of the transformer 120 which is an isolation transformer. The amplifier 118 also serves to buffer the oscillator 116 from the transformer 120. The isolation transformer 120 has a turns ratio sufficient to step up the amplified sinusoidal signal to drive the transducer 112 from the secondary winding of the transformer 120.

Various other embodiments and variations of the present invention are also contemplated. And although the brush 16 is assembled with an enamel wire and the vibrational energy source described in the preferred embodiment is a DC motor driving an eccentrically mounted weight to produce vibrations within the interproximal brush plaque remover various other combinations to provide vibratory energy to the brush 16 may be developed by one skilled in this art. Thus, the scope of the present invention is not to be limited to the above description but is to be defined according to the claims which follow:

What is claimed:

1. In an apparatus for removal of dental plaque from in between adjacent teeth having a dental hand piece integrally attached to an arm adapted for insertion into a human mouth, a dental brush having a spine supported substantially perpendicular from said arm, said hand piece imparting an interproximal mechanical action through contact of said brush with dental surfaces in between said adjacent teeth, first means in said hand piece for mechanically moving the dental brush, the improvement comprising said dental brush having a conical shape, said conical shape being defined by a cross-section representing a triangle having an apex angle of approximately thirty degrees and wherein said brush has means for contouring its shape and wherein said first means is a vibrating means in said hand piece adapted for mechanically vibrating the dental brush small distances, said brush having a spine adapted for insertion in between adjacent teeth, said brush having bristles attached to said spine, said bristles being sufficiently soft to splay into pockets, junctures and furca in between adjacent teeth, said bristles being further adapted for sweeping a plenum interproximally located between said adjacent teeth.

2. An apparatus for removal of dental plaque as in claim 1, wherein said dental brush comprises a replaceable dental brush detachably mounted onto said arm via said spine and wherein said means for contouring said brush is a malleable spine.

3. An apparatus for removal of dental plaque as in claim 2 wherein said dental brush is comprised of soft plastic bristles spirally attached to said malleable spine whereby said bristles are contourable and vary in length.

4. An apparatus for removal of dental plaque as in claim 1 wherein said vibrating first means comprises a motor adapted to vibrate said dental brush small distances from 0.3 mm to 3.0 mm.

5. An apparatus for removal of dental plaque as in claim 4 where said spine is comprised of soft wire.

6. An apparatus for removal of dental plaque as in claim 5 further comprising second means for said dental brush to sweep an interproximal plenum between said teeth.

7. An apparatus for removal of dental plaque as in claim 6 wherein said second means comprises said spine being made of twisted wire, said twisted wire being sufficiently flexible and bendable to be curled to a contour of a tooth upon insertion and upon mechanical vibration between two teeth whereby plaque is swept away.

8. An apparatus for removal of dental plaque according to claim 4 wherein said brush has an outer contour and further comprises a means for molding said outer contour, said adjacent teeth having an interproximal cavity with a left contour and a right contour, said brush further comprising means for adapting said outer contour to said first and second contours.

9. An apparatus according to claim 8 wherein said means for molding said outer contour comprises an elongated member made of at least two strands of thin soft wire twisted about a central axis, said strands having therein between them bristles which comprise said brush.

10. An apparatus according to claim 9 wherein said brush is at least 10 millimeters long.

* * * * *